(12) United States Patent
Tal et al.

(10) Patent No.: US 9,375,216 B2
(45) Date of Patent: Jun. 28, 2016

(54) DIRECTION REVERSING VASCULAR TREATMENT DEVICE

(75) Inventors: Michael G. Tal, Woodbridge, CT (US); John P. Marano, Madison, CT (US)

(73) Assignee: Vascular Insights, LLC, Quincy, MA (US)

(*) Notice: Subject to any disclaimer, the term of this patent is extended or adjusted under 35 U.S.C. 154(b) by 0 days.

(21) Appl. No.: 13/295,495

(22) Filed: Nov. 14, 2011

(65) Prior Publication Data
US 2012/0130410 A1    May 24, 2012

Related U.S. Application Data

(60) Provisional application No. 61/413,895, filed on Nov. 15, 2010.

(51) Int. Cl.
*A61B 17/22* (2006.01)
*A61B 17/12* (2006.01)
*A61B 17/3207* (2006.01)

(52) U.S. Cl.
CPC ....... *A61B 17/12013* (2013.01); *A61B 17/3207* (2013.01); *A61B 17/320758* (2013.01); *A61B 2017/320733* (2013.01)

(58) Field of Classification Search
CPC .............. A61B 17/3207; A61B 17/12013; A61B 17/320758; A61B 17/22; A61B 2017/320733
USPC .......... 606/159, 194, 170, 180, 41, 79, 181, 606/200; 128/898
See application file for complete search history.

(56) References Cited

U.S. PATENT DOCUMENTS

| | | | |
|---|---|---|---|
| 2,212,477 A | 8/1940 | Lefferts | |
| 3,405,712 A | 10/1968 | Pierick | |
| 3,530,492 A | 9/1970 | Ferber | |
| 3,631,847 A | 1/1972 | Hobbs, II | |
| 3,633,566 A | 1/1972 | Grabhorn | |
| 4,278,085 A | 7/1981 | Shim | |
| 4,403,611 A | 9/1983 | Babbitt et al. | |
| 4,577,514 A | 3/1986 | Bradley et al. | |
| 4,586,921 A | 5/1986 | Berson | |
| 4,728,319 A | 3/1988 | Masch | |

(Continued)

FOREIGN PATENT DOCUMENTS

| CA | 2405273 | 4/2001 |
|---|---|---|
| CN | 2148536 | 12/1993 |

(Continued)

OTHER PUBLICATIONS

International Search Report and Written Opinion dated May 23, 2012 for PCT Application No. PCT/US2011/060859.
International Search Report and Written Opinion dated May 30, 2012 for PCT Application No. PCT/US2011/060860.
International Search Report and Written Opinion dated May 30, 2012 for PCT Application No. PCT/US2011/060855.
International Search Report for PCT/US2007/078367.
Written Opinion for PCT/US2007/078367.
Williams et al. "Sclerosant Treatment of Varicose Veins and Deep Vein Thrombosis," Archives of Surgery, vol. 119, No. 11, Nov. 1984.
International Search Report for PCT/US04/15858.

(Continued)

*Primary Examiner* — David C Eastwood
*Assistant Examiner* — Tin Nguyen
(74) *Attorney, Agent, or Firm* — Baker & Hostetler LLP (57) ABSTRACT

An apparatus for performing a vascular treatment includes an intraluminal member that is controllingly moved during the vascular treatment. The intraluminal member of the vascular treatment device can be connected to a motor. The rotation direction of the intraluminal member can be reversed to reduce the incidence and duration of vein entanglement during a vascular ablation procedure. Reversal of direction could occur automatically, or in response to a sensor such as a load sensor provided as part of the motorized drive system.

26 Claims, 5 Drawing Sheets

(56) References Cited

U.S. PATENT DOCUMENTS

| | | |
|---|---|---|
| 4,854,325 A | 8/1989 | Stevens |
| 4,867,156 A | 9/1989 | Stack et al. |
| 4,876,109 A * | 10/1989 | Mayer et al. .................. 427/2.24 |
| 4,906,236 A | 3/1990 | Alberts et al. |
| 4,936,845 A | 6/1990 | Stevens |
| 5,022,399 A | 6/1991 | Biegeleisen |
| 5,047,013 A | 9/1991 | Rossdeutscher |
| 5,074,871 A | 12/1991 | Groshong |
| 5,087,244 A | 2/1992 | Wolinsky et al. |
| 5,087,265 A | 2/1992 | Summers |
| 5,135,517 A | 8/1992 | McCoy |
| 5,176,646 A | 1/1993 | Kuroda |
| 5,269,794 A | 12/1993 | Rexroth |
| 5,330,481 A | 7/1994 | Hood et al. |
| 5,370,653 A | 12/1994 | Cragg |
| 5,415,636 A | 5/1995 | Forman |
| 5,449,351 A | 9/1995 | Zohmann |
| 5,549,601 A | 8/1996 | McIntyre et al. |
| 5,578,014 A | 11/1996 | Erez et al. |
| 5,611,357 A | 3/1997 | Suval |
| 5,628,730 A | 5/1997 | Shapland et al. |
| 5,632,755 A | 5/1997 | Nordgren et al. |
| 5,675,228 A | 10/1997 | O'Bryan |
| 5,707,355 A | 1/1998 | Zimmon |
| 5,709,657 A | 1/1998 | Zimmon |
| 5,716,366 A | 2/1998 | Yates |
| 5,766,191 A | 6/1998 | Trerotola |
| 5,776,153 A | 7/1998 | Rees |
| 5,836,905 A | 11/1998 | Lemelson et al. |
| 5,882,329 A | 3/1999 | Patterson et al. |
| 5,902,266 A | 5/1999 | Leone et al. |
| 5,908,395 A | 6/1999 | Stalker et al. |
| 5,911,700 A | 6/1999 | Mozsary et al. |
| 5,921,963 A | 7/1999 | Erez et al. |
| 5,976,164 A | 11/1999 | Bencini et al. |
| 6,048,332 A | 4/2000 | Duffy et al. |
| 6,090,118 A | 7/2000 | McGuckin, Jr. |
| 6,159,196 A | 12/2000 | Ruiz |
| 6,165,187 A | 12/2000 | Reger |
| 6,171,234 B1 | 1/2001 | White et al. |
| 6,193,735 B1 | 2/2001 | Stevens |
| 6,193,736 B1 | 2/2001 | Webler et al. |
| 6,231,518 B1 | 5/2001 | Grabek et al. |
| 6,258,087 B1 | 7/2001 | Edwards et al. |
| 6,261,272 B1 | 7/2001 | Gross et al. |
| 6,273,882 B1 | 8/2001 | Whittier et al. |
| 6,290,675 B1 | 9/2001 | Vujanic et al. |
| D450,843 S | 11/2001 | McGuckin, Jr. et al. |
| 6,346,095 B1 | 2/2002 | Gross et al. |
| 6,369,039 B1 | 4/2002 | Palasis et al. |
| 6,402,745 B1 | 6/2002 | Wilk |
| 6,443,929 B1 | 9/2002 | Kuracina et al. |
| 6,482,215 B1 | 11/2002 | Shiber |
| 6,484,727 B1 | 11/2002 | Vaska et al. |
| 6,520,928 B1 | 2/2003 | Junior |
| 6,544,221 B1 | 4/2003 | Kokish et al. |
| 6,547,776 B1 | 4/2003 | Gaiser et al. |
| 6,575,932 B1 | 6/2003 | O'Brien et al. |
| 6,602,264 B1 | 8/2003 | McGuckin, Jr. |
| 6,673,025 B1 | 1/2004 | Richardson et al. |
| 6,679,886 B2 | 1/2004 | Weikel et al. |
| 6,733,473 B1 | 5/2004 | Reifart et al. |
| 6,824,550 B1 | 11/2004 | Noriega et al. |
| 6,824,551 B2 | 11/2004 | Trerotola |
| 6,852,118 B2 | 2/2005 | Shturman et al. |
| 7,025,774 B2 | 4/2006 | Freeman et al. |
| 7,083,643 B2 | 8/2006 | Whalen et al. |
| 7,108,704 B2 | 9/2006 | Trerotola |
| 7,211,073 B2 | 5/2007 | Fitzgerald et al. |
| 7,285,126 B2 | 10/2007 | Sepetka et al. |
| 7,402,155 B2 | 7/2008 | Palasis et al. |
| 7,670,328 B2 | 3/2010 | Miller |
| 7,713,231 B2 | 5/2010 | Wulfman |
| 7,862,575 B2 | 1/2011 | Tal |
| 7,967,834 B2 | 6/2011 | Tal et al. |
| 8,029,491 B2 | 10/2011 | Aboul-Hosn et al. |
| 8,038,664 B2 | 10/2011 | Miller et al. |
| 8,052,645 B2 | 11/2011 | Slate et al. |
| 2001/0004700 A1 * | 6/2001 | Honeycutt et al. ............ 606/159 |
| 2002/0010418 A1 | 1/2002 | Lary et al. |
| 2002/0077589 A1 | 6/2002 | Tessari |
| 2002/0077594 A1 | 6/2002 | Chien et al. |
| 2002/0188276 A1 | 12/2002 | Evans et al. |
| 2003/0004568 A1 | 1/2003 | Ken et al. |
| 2003/0045860 A1 | 3/2003 | Leu |
| 2003/0120256 A1 | 6/2003 | Lary et al. |
| 2003/0225435 A1 * | 12/2003 | Huter et al. .................. 606/200 |
| 2004/0092967 A1 | 5/2004 | Sancoff et al. |
| 2004/0147934 A1 * | 7/2004 | Kiester ......................... 606/80 |
| 2004/0220519 A1 | 11/2004 | Wulfman et al. |
| 2004/0254566 A1 | 12/2004 | Plicchi |
| 2005/0055040 A1 * | 3/2005 | Tal ................................ 606/159 |
| 2005/0055041 A1 | 3/2005 | Woods |
| 2005/0096642 A1 | 5/2005 | Appling et al. |
| 2005/0165354 A1 | 7/2005 | Schwartz et al. |
| 2006/0015169 A1 | 1/2006 | Letort |
| 2006/0095015 A1 | 5/2006 | Hobbs et al. |
| 2006/0217692 A1 | 9/2006 | Neuberger |
| 2006/0224110 A1 | 10/2006 | Scott et al. |
| 2007/0112308 A1 | 5/2007 | Kay et al. |
| 2007/0239140 A1 | 10/2007 | Chechelski et al. |
| 2007/0282359 A1 | 12/2007 | Tal |
| 2008/0009791 A1 | 1/2008 | Cohen et al. |
| 2008/0243068 A1 | 10/2008 | Ramzipoor et al. |
| 2008/0300571 A1 | 12/2008 | LePivert |
| 2008/0300574 A1 | 12/2008 | Belson et al. |
| 2009/0137906 A1 | 5/2009 | Maruyama et al. |
| 2009/0222003 A1 | 9/2009 | Otley |
| 2009/0270889 A1 | 10/2009 | Tal et al. |
| 2010/0069760 A1 | 3/2010 | Tang |
| 2010/0125276 A1 * | 5/2010 | Palermo ......................... 606/80 |
| 2010/0268076 A1 | 10/2010 | Gat et al. |
| 2010/0274178 A1 | 10/2010 | LePivert |
| 2011/0066142 A1 | 3/2011 | Tal |
| 2012/0130410 A1 | 5/2012 | Tal et al. |
| 2012/0197200 A1 | 8/2012 | Belson |
| 2012/0265168 A1 | 10/2012 | Horowitz et al. |

FOREIGN PATENT DOCUMENTS

| | | |
|---|---|---|
| DE | 10059742 | 6/2002 |
| EP | 0501081 | 9/1992 |
| FR | 2651682 | 3/1991 |
| JP | 2003-523803 A | 8/2003 |
| JP | 2009-078150 A | 4/2009 |
| JP | 2010-503479 A | 2/2010 |
| WO | WO 97/14362 | 4/1997 |
| WO | WO 00/07500 A1 | 2/2000 |
| WO | WO 01/54754 A1 | 8/2001 |
| WO | WO 2008/033983 | 3/2008 |
| WO | WO 2009/109967 A1 | 9/2009 |
| WO | WO 2012/068162 | 5/2012 |
| WO | WO 2012/068165 | 5/2012 |
| WO | WO 2012/068166 | 5/2012 |
| WO | WO 2008/033983 A1 | 3/2015 |

OTHER PUBLICATIONS

Written Opinion for PCT/US04/15858.
International Preliminary Report on Patentability dated Jun. 5, 2013 for PCT Application No. PCT/US2011/060855.
International Preliminary Report on Patentability dated May 16, 2013 for PCT Application No. PCT/US2011/060859.
International Preliminary Report on Patentability dated May 30, 2013, for PCT Application No. PCT/US2011/060860.
International Preliminary Report on Patentability dated May 7, 2013, for PCT Application No. PCT/US2011/060859.
International Preliminary Report on Patentability dated Jun. 3, 2013, for PCT Application No. PCT/US2011/060855.

* cited by examiner

DIRECTION REVERSING VASCULAR TREATMENT DEVICE

CROSS-REFERENCE TO RELATED APPLICATIONS

This application claims the benefit of U.S. Provisional Application No. 61/413,895, filed on Nov. 15, 2010, the disclosure of which is hereby incorporated by reference in its entirety.

BACKGROUND OF THE INVENTION

1. Field of the Invention

This specification relates to the field of vascular treatment.

2. Description of the Related Art

Sclerotherapy can be used to treat blood vessels, blood vessel malformations, and similar problems in other body systems, such as the lymphatic system, and has been used in various forms for over 150 years. In its more modern form, sclerotherapy has been used since the 1960's, in Europe, for treating various vein conditions such as; varicose veins, reticular veins, spider veins of the leg, and also some fine facial veins.

Sclerotherapy can be used to treat these conditions by instigating vascular fibrosis and obliteration in response to irreversible endothelial cellular destruction and exposure of the underlying subendothelial cell layer. This destruction is usually caused by the injection of a sclerosant into the vein. However, if the injected sclerosant is too weak, there may be no endothelial injury at all. If the sclerosant is a little stronger, the varicose vessel is damaged, but recanalization occurs and an incompetent pathway for retrograde blood flow persists. Finally, if the injected sclerosant is too strong, the varicose vessel endothelium is destroyed, but adjacent vessels that are not targeted for treatment may also be damaged by the sclerosant.

The requirement for an ideal strength of the sclerosant is complicated by the constant flow of blood through the vein that is being treated. This flow simultaneously dilutes, and thereby weakens, the sclerosant, while also transporting the sclerosant to other parts of the vascular system.

Thus, improved methods and devices for treating the vascular system are desired.

SUMMARY OF THE INVENTION

Some embodiments relate to a vascular treatment apparatus. The apparatus can include, for example, an elongated intraluminal member shaped and dimensioned for passage through blood vessels of a subject. The intraluminal member can include, for example, a proximal end and a distal end. The apparatus can further include a motorized drive system coupled to the intraluminal member. The motorized drive system can, in some embodiments, reverse the direction of rotation of the intraluminal member.

In some embodiments of the apparatus, the motorized drive system can be, for example, a reversible motor, a kinematic chain, or a gearbox. In some embodiments of the apparatus, the motorized drive system can rotationally oscillate the intraluminal member. In some embodiments, the motorized drive system can oscillate the intraluminal member in a manner configured to inhibit entanglement of the intraluminal member with the vein, or can reverse the direction of rotation when a load threshold is reached or exceeded.

Some embodiments relate to a method for vascular treatment. The method can include, for example, advancing an elongated intraluminal member from an access site and into the vein. The method may comprise rotating the intraluminal member or portion thereof in a first direction, and reversing the direction of rotation of the intraluminal member or portion thereof. In some embodiments of the method, the reversal of a direction of rotation occurs when a threshold load is met or exceeded. The rotation reversal can, for example, inhibit entanglement of the intraluminal member with the vein.

In another embodiment, a vascular treatment apparatus comprises an elongated intraluminal member shaped and dimensioned for passage through blood vessels of a subject, the intraluminal member including a proximal end and a distal end. At least a first motor is coupled to the intraluminal member to move the intraluminal member, a motor drive circuit is coupled to the motor; and a load sensor is coupled to the motor drive circuit. The motor drive circuit may stop or reverse direction of the motor in response to a sensed load.

In one specific application, the apparatus and methods may be applied to permanently occluding veins. In these embodiments, the intraluminal member may have a portion that can produce damage to the inner vein wall. The apparatus may further comprise a source of sclerosant and a fluid channel between the source of sclerosant and the distal end of the elongated intraluminal member.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DETAILED DESCRIPTION OF THE PREFERRED EMBODIMENT

The following description and examples illustrate preferred embodiments of the present invention in detail. Those of skill in the art will recognize that there are numerous variations and modifications of this invention that are encompassed by its scope. Accordingly, the description of a preferred embodiment should not be deemed to limit the scope of the present invention. In this description, reference is made to the drawings wherein like parts are designated with like numerals throughout.

Figure 1:
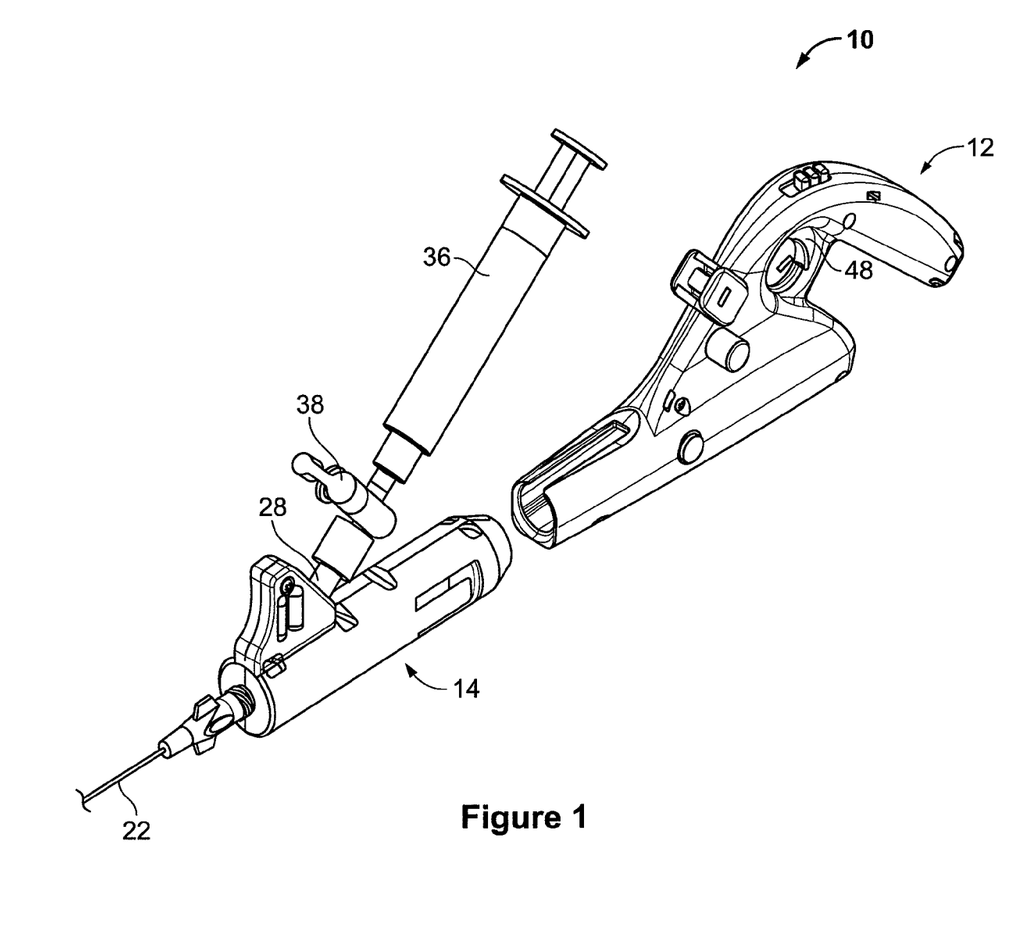
FIG. 1 shows an embodiment of an assembly of a vascular treatment device.

FIG. 1 depicts a perspective view of one embodiment of exemplary components of a vascular treatment device 10. These components can be configured to provide a range of functionalities to the vascular treatment device 10. In some embodiments, a vascular treatment device 10 can include features configured for stimulating vascular ablation, such as, for example, an intraluminal member 22, a motorized drive system, including, for example, a motor, and/or control features and/or features configured for delivering liquid sclerosant. In some embodiments described further below, the intraluminal member comprises a wire surrounded by a sheath, and the wire is rotatable within the sheath. The space between the sheath and the wire can be used as a passage to inject sclerosant as the wire rotates, and the distal end of the wire forms a vein wall disruptor.

In general, the vascular treatment device 10 of FIG. 1 is utilized by introducing the intraluminal member into a vein of a subject, where the vein is to be ablated in a treatment for varicose veins for example. The distal end of the wire is extended from the distal end of the sheath, and the wire is rotated or otherwise moved to damage the endothelium lining the inside surface of the vein. Sclerosant is also injected to the region of damage through the sheath that forms an outer portion of the intraluminal member 22. The combination of endothelium damage plus the sclerosant provides a highly effective vascular ablation procedure with a minimum amount of injected sclerosant.

As depicted in FIG. 1, a vascular treatment device can include a handle 12 and a cartridge 14. As explained below in greater detail, each of the handle 12 and cartridge 14 can include features configured for stimulating vascular ablation and/or for delivering liquid sclerosant. In one embodiment, and as depicted in FIG. 1, the handle 12 and the cartridge 14 can comprise separate pieces. In another embodiment, a handle 12 and a cartridge 14 can comprise an integrated component. A person of skill in the art will recognize that the present disclosure is not limited to a specific configuration of the handle 12 and cartridge 14 but broadly includes the range of functions and uses of a vascular therapy device.

As further depicted in FIG. 1, the cartridge 14 can be, for example, sized and shaped to engagingly connect to the handle 12. In one embodiment, and as shown in FIG. 1, this engaging connection can be achieved by fitting features of the handle 12 to features of the cartridge 14.

Figure 2A:
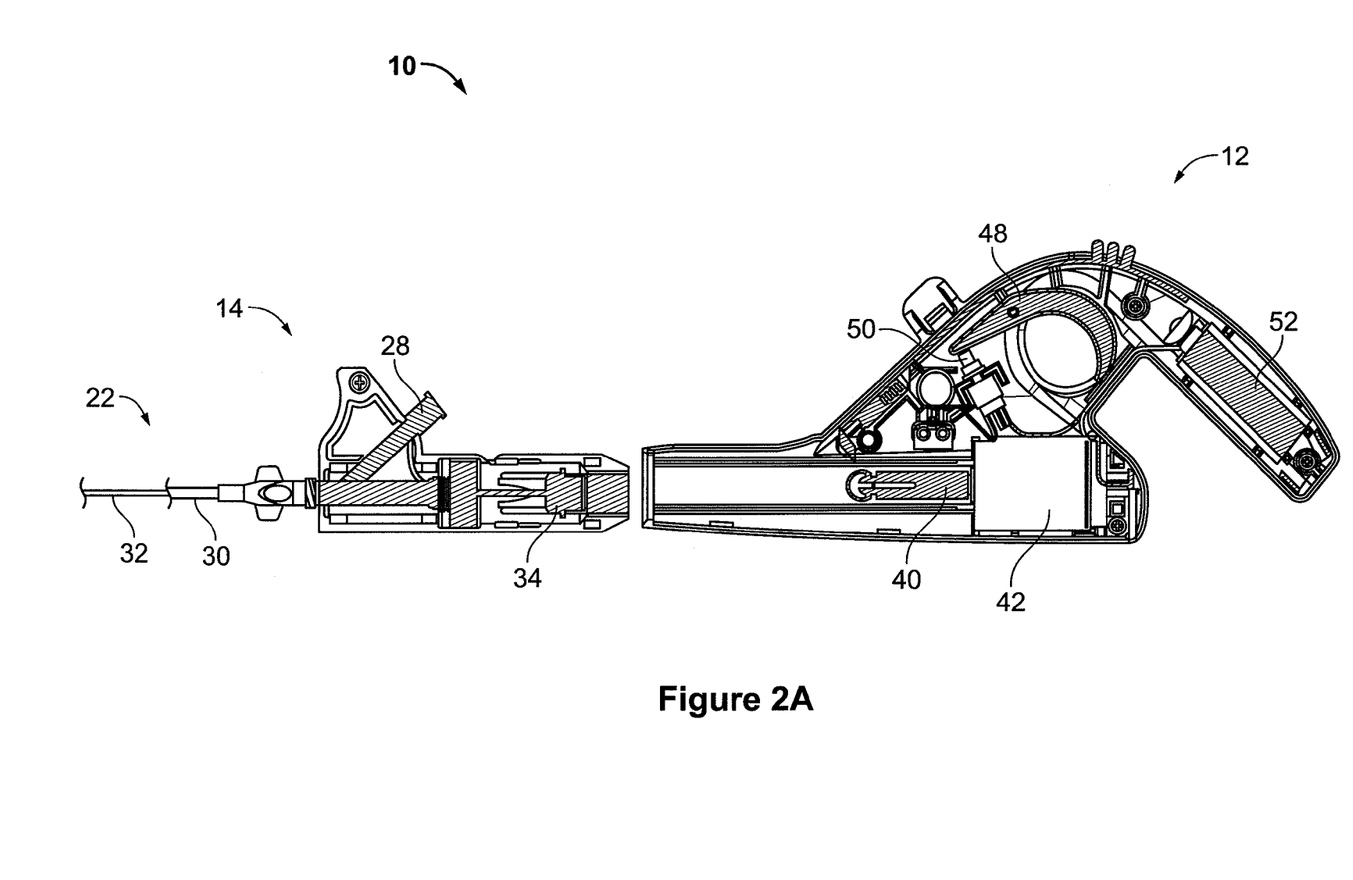
FIG. 2A illustrates a longitudinal cross-sectional view of the embodiment illustrated in FIG. 1.

FIG. 2 depicts a side cross-section view of the vascular treatment device 10 of FIG. 1. The vascular treatment device 10 depicted in FIG. 2 comprises the same features discussed in relation to FIG. 1. Referring now to both FIGS. 1 and 2, the cartridge 14 may include a sheath 30 affixed to and extending from the cartridge 14, a wire 32, and a coupling 34. The wire 32 can be, for example, fixed to the coupling 34. A person of skill in the art will recognize that the wire 32 can be affixed to the coupling 34 through a variety of techniques and methods. A person of skill in the art will further recognize that the wire 32 can be affixed to a range of features of a vascular treatment device 10 configured for driving the wire 32.

The wire 32 (and surrounding sheath) can comprise a variety of lengths. In some embodiments, a wire 32 can have a length matching the needs of the procedure. In some embodiments, a wire 32 can have a length, for example, of up to 10 cm, up to 25 cm, up to 75 cm, or up to 150 cm.

The sheath 30 can be configured to define a lumen through which the wire 32 runs, and can be configured to allow independent motion of the wire within the sheath. The sheath 30 can have a variety of inner and outer diameters. In some embodiments, the sheath 30 can have an inner diameter ranging from approximately 0.022 inches to 0.048 inches. In some embodiments, the sheath 30 can have an outer diameter ranging from approximately 0.025 inches to 0.051 inches. In some embodiments, the outer diameter of the sheath 30 can be in the range that is, for example, consistent with the inner diameter of standard needles or vascular sheaths used for used for insertion of vascular catheters.

The sheath 30 may also include external markings at regular intervals which may guide the user to monitor the insertion or removal speed of the intraluminal member 22.

Some embodiments of a vascular treatment device 10 can be configured for use with injectant. In some embodiments, the cartridge 14 can be configured for holding an injectant such as sclerosant in a syringe 36 attached to the cartridge 14 at a coupler 28. Some embodiments of a vascular treatment device 10 and/or a cartridge 14 configured for use in connection with an injectant can be, for example, configured with valves and connectors to facilitate such use. In some embodiments, a syringe 36 can, for example, connect to a stopcock 38 on a cartridge 14. The stopcock 38 shown in FIG. 2 can be configured to allow the removal and/or attachment of a syringe to the vascular treatment device 10 during a procedure. In some embodiments, a stopcock 38 can be configured to allow reloading of fluid and/or exchanging of containers to, for example, change the injectant or the concentration of the injectant. In some embodiments, the stopcock 38 can be configured to provide additional functionality, such as, for example, mixing or aerating the injectant. The output of the coupler 28 is in fluid communication with the space between the sheath 30 and the wire 32 so that the injectant can be pushed along this space to the distal end of the wire and sheath where the injectant (e.g. sclerosant) exits the sheath when installed in the vein.

Figure 2B:
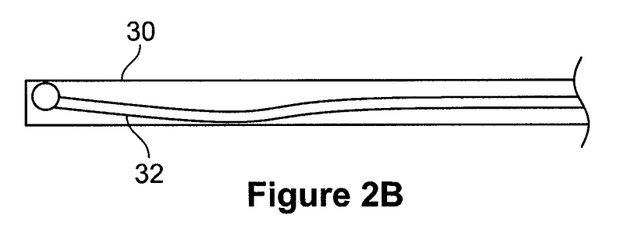
FIG. 2B illustrates the distal ends of the wire and sheath of FIG. 2A with the distal end of the wire within the sheath.
Figure 2C:
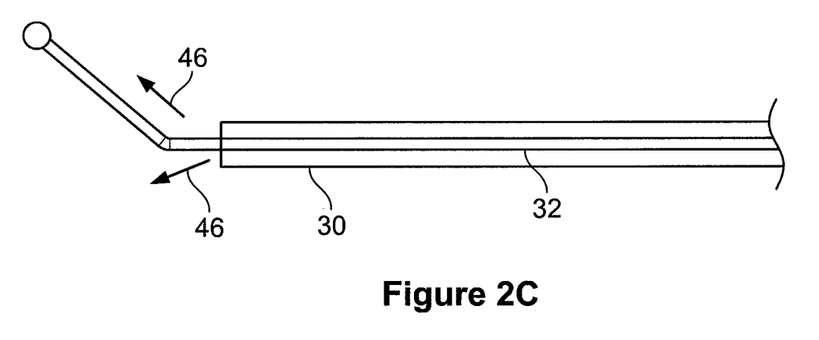
FIG. 2C illustrates the distal ends of the wire and sheath of FIG. 2A with the distal end of the wire extending out from the end of the sheath.

In use, the sheath 30 with the wire 32 inside may be introduced into the vein prior to coupling the cartridge 14 to the handle 12. At this time, the wire 32 may be fully enclosed by the sheath 30 as shown in FIG. 2B. After introduction, the cartridge 14 can be inserted into the handle 12, and the coupler 34 can engage a mating coupler 40 in the handle. The coupler 34 in the cartridge which is attached to the wire 32 may be slidable within the cartridge 14, so that when the coupler 34 in the cartridge is forced into engagement with the coupler 40, the distal end of the wire 32 is pushed out of the sheath 30, as shown in FIG. 2C. This exposes a portion of the wire 32 that is configured to damage the endothelium on the inner surface of the vein. The coupler 40 in the handle 12 is attached to the shaft of a motor 42 in the handle that may rotate the coupler 40, mated coupler 34, and attached wire 32 to scrape and damage the inner wall of the vein. During this process, sclerosant may be forced down the sheath, to exit the sheath in the region near the distal end of the wire 32, as shown by arrows 46 in FIG. 2C.

Motor rotation may be controlled by a trigger 48 in the handle that depresses and releases a switch 50 to start and stop motor rotation. The handle 12 may further include a power source for the motor such as battery 52. Embodiments of vascular treatment devices such as illustrated in FIGS. 1 through 2C are further described in U.S. Pat. Nos. 7,862,575 and 7,967,834 which are incorporated herein by reference in their entireties.

Although vascular ablation treatments using the above described vascular treatment device have shown dramatic improvement over prior vascular ablation methods, it has been found that the drive system illustrated in FIG. 2A is sometimes not optimal. For example, the distal end of the wire 32 can sometimes catch on the inner vein wall, twisting the vein and entangling the wire and the vein. When this occurs, the operator of the device may need to stop the procedure to release the wire from the vein. This issue may be caused by insufficient control or variation of motor motion during the procedure, a problem that is addressed by the embodiments described below with respect to FIGS. 3, 4, and 5.

Figure 3:
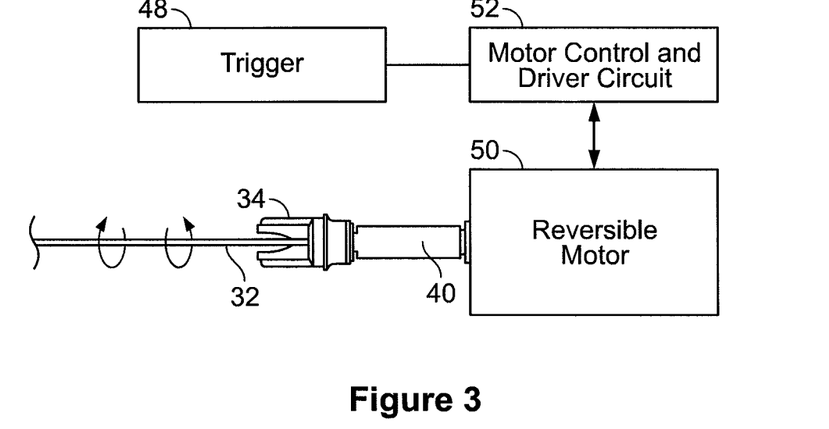
FIG. 3 shows a schematic view of a motion system for a vascular treatment device that incorporates a reversible motor.
Figure 4:
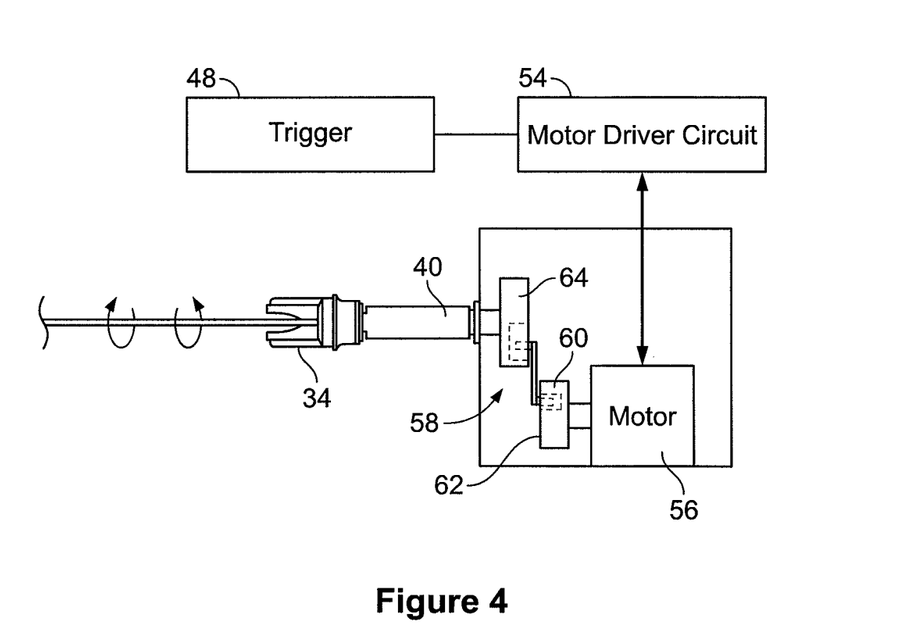
FIG. 4 shows a schematic view of a motion system for a vascular treatment device that incorporates an oscillating gear system.
Figure 5:
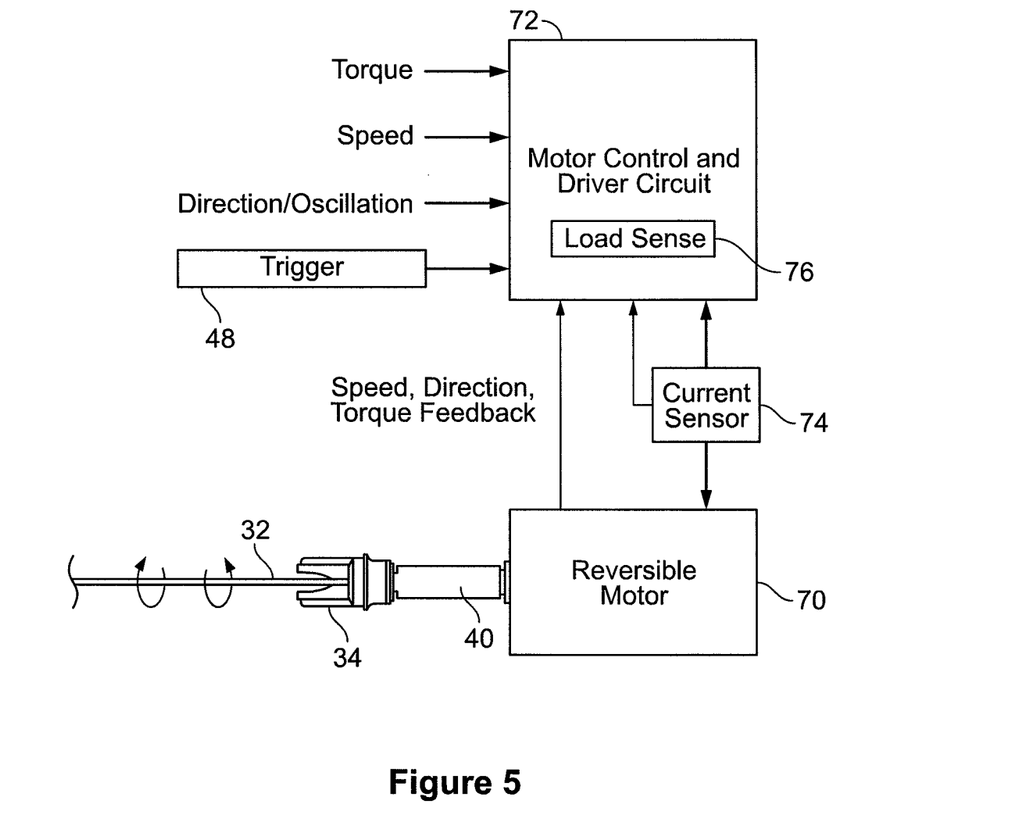
FIG. 5 shows a schematic view of a motion system for a vascular treatment device that incorporates a reversible motor with load sensing and additional control functions.

FIG. 3 illustrates one embodiment of a wire 32 drive system that helps resolve these problems. In FIGS. 3, 4, and 5, many components of the cartridge 14 and handle 12 are omitted for clarity, focusing only on the drive system for wire 32. Couplers 34 and 40 are shown. In the embodiment of FIG. 3, a motor 50 used to drive the wire 32 is a reversible motor. The motor 50 is controlled by a motor control and driver circuit 52 that is configured to periodically change the direction of rotation of the wire 32. Such a change in direction can be performed at defined time intervals such as one a second, ten times a second, etc., or the change in direction can be performed after a set number of rotations such as every five rotations, or with every rotation, or with fractions of a rotation if desired. Random or pseudo-random timing of rotation changes is also possible. Thus, a variety of rotational oscillation motions can be programmed or hard wired into the motor control and driver circuit 52. Such motors and motor control circuits are well known and commercially available, and can be used in place of the motor 42 and single direction rotation of FIG. 2. With these direction rotations, entanglement with the vein is less likely, and if it does occur, the next direction reversal is likely to free the wire from the vein.

FIG. 4 depicts a motorized drive system comprising a trigger 48, a motor driver circuit 54, a motor 56, and a kinematic chain 58 connecting the motor 56 to the coupler 40. The kinematic chain 58 can comprise, for example, an assemblage of links and joints interconnected so as to provide a desired output in response to desired input. In some embodiments, the kinematic chain 58 can comprise one or several gears, one or several rigid linked members, one or several flexible linked members, or any other desired feature. In some embodiments, the kinematic chain 58 can be configured to translate a single direction motor 56 output into rotational oscillation of the wire 32.

FIG. 4 depicts one specific kinematic chain 58 comprising a first wheel 60, a link 62, and a second wheel 64. In some embodiments, the motor 56 can rotate the first wheel 60 about the axis of the motor driven shaft. A first end of the link 62 can be rotationally connected to a portion of the first wheel 60, and a second end of the link 62 can be rotationally and slidingly connected with a portion of the second wheel 64. The combination of the rotational connection of the first end of the link 62 to the first wheel 60, and the rotational and sliding connection of the second end of the link 62 to the second wheel 64 can allow conversion of the single direction rotational input of the driven shaft of the motor to rotationally oscillating output of the motorized drive system output. Although one specific kinematic chain 58 is described herein, a person of skill in the art will recognize that a variety of kinematic chains can be used in connection with the motorized drive system to achieve the desired movement of the wire 32. The motorized drive system of FIG. 4 utilizes a simpler and less expensive motor and motor drive circuit compared to the system of FIG. 3, with the addition of the mechanical components of the kinematic chain 58.

FIG. 5 depicts a motorized drive system comprising a trigger 48, a motor control and driver circuit 72, and a reversible motor 70. In addition to these features, FIG. 5 depicts a load sensor 76 that may be incorporated into the motor control and driver circuit 72. The load sensor 76 can be configured to detect the motor load based on inputs from an output current sensor 74 that senses the current being used to drive the motor and/or other sensor signals such as speed and torque signals that may be routed to the motor control and drive circuit 72 from sensors integral to the motor 70. For example, the load sensor may determine that the current to the motor has exceeded a threshold, that the torque output has exceeded a threshold, or that the speed of rotation has slowed below a threshold. It will be appreciated that the load sensor, 76, current sensor 74 or other motor parameter sensors can be incorporated into the motor 70, the motor control and driver circuit 72, be standalone components, or have portions thereof distributed in any of these or other locations. The load sensor 76 can comprise software, hardware, or a combination of hardware and software.

The motor control and driver circuit 72 can be configured to control the motor based in part on signals generated by the motor load sensor 76. In some embodiments, the motor control and driver circuit 72 may speed up the rotation rate of the motor 70, slow down the rotation rate of the motor 70, or reverse the direction of rotation of the motor 70 in response to signals generated by the motor load sensor 76. In one embodiment, the motor control and driver circuit 72 can be configured to reverse the direction of rotation of the motor 72 when the motor load sensor 76 detects a motor load which meets or exceeds a load threshold. In some embodiments, this load threshold can, for example, correspond to a condition with the treated vessel, such as, for example, entanglement of the wire 32 in vein tissue, over penetration of the wire 32 into vein tissue, or other conditions. Advantageously, the reversing of the direction of rotation of the motor 70, and thereby reversing the direction of rotation of the wire 32 can minimize the severity and duration of, and/or prevent entanglement of the wire 32 with the vein.

In some embodiments, the motor control and driver circuit 72 is user programmable with a variety of motor control options. The user may, for example, be able to select a rotation speed, a desired torque value or torque limit during the procedure, the direction of rotation, and whether and how quickly the wire should oscillate back and forth with reversing rotations or rotate in one direction only. The motorized drive system can, for example, be programmable to rotate the wire 32 at any rate between approximately 500 to 5,000 rpm, and reverse direction at any rate between every half rotation to every 500 rotations.

The device could include switches or a keypad for such programmable control, or may have an input/output port for interfacing to a computer for download of configuration choices. The behavior of the motor control and driver circuit 72 in response to sensor inputs related to load, speed, etc. could also be programmable, or may be fixed at manufacture.

The foregoing description details certain embodiments of the devices and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. Furthermore, although the above description has focused on the application of the principles discussed to vein ablation procedures, the features set forth above could be applied to a variety of vascular treatments.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A method of treating a vein comprising the following steps:
    advancing an elongated intraluminal member from an access site and into a vein;
    rotating the intraluminal member or portion thereof in a first direction with a motorized drive system coupled to the intraluminal member or portion thereof, the motorized drive system comprising a motor drive circuit and a motor; and
    periodically changing the direction of rotation of the intraluminal member or portion thereof to perform rotational oscillation by periodically changing the direction of rotation of the motorized drive system,
    wherein the periodic changing of the direction of rotation of the intraluminal member occurs at random time intervals, and
    wherein the rotational oscillation of the intraluminal member or portion thereof damages an inner wall of the vein, and inhibits entanglement of the intraluminal member or portion thereof with the inner wall of the vein.

2. The method of claim 1, wherein the direction of rotation changes when a load threshold is met or exceeded.

3. The method of claim 1, wherein the motor comprises a reversible motor.

4. The method of claim 1, wherein the drive system comprises a kinematic chain.

5. The method of claim 1, wherein the drive system comprises a gearbox.

6. The method of claim 3, further comprising periodically reversing a rotation direction of the reversible motor.

7. The method of claim 6, further comprising programming a motor control and the motor drive circuit to perform the periodic reversal of the rotation direction of the reversible motor.

8. The method of claim 1, further comprising injecting sclerosant into the vein and onto the inner wall of the vein.

9. The method of claim 1, wherein a distal end of the intraluminal member comprises a vein wall disruptor.

10. A method of treating a vein comprising the following steps:
    advancing an elongated intraluminal member from an access site and into a vein;
    rotating the intraluminal member or portion thereof in a first direction with a motorized drive system coupled to the intraluminal member or portion thereof, the motorized drive system comprising a motor drive circuit and a motor; and
    periodically changing the direction of rotation of the intraluminal member or portion thereof to perform rotational oscillation by periodically changing the direction of rotation of the motorized drive system,
    wherein the periodic changing of the direction of rotation of the intraluminal member occurs for every full rotation of the intraluminal member or portion thereof, and
    wherein the rotational oscillation of the intraluminal member or portion thereof damages an inner wall of the vein, and inhibits entanglement of the intraluminal member or portion thereof with the inner wall of the vein.

11. The method of claim 10, wherein the periodic changing of the direction of rotation of the intraluminal member occurs after a set number of rotations or fraction thereof.

12. The method of claim 10, wherein the motor comprises a reversible motor.

13. The method of claim 10, wherein the drive system comprises a kinematic chain.

14. The method of claim 10, wherein the drive system comprises a gearbox.

15. The method of claim 12, further comprising periodically reversing a rotation direction of the reversible motor.

16. The method of claim 15, further comprising programming a motor control and the motor drive circuit to perform the periodic reversal of the rotation direction of the reversible motor.

17. The method of claim 10, further comprising injecting sclerosant into the vein and onto the inner wall of the vein.

18. The method of claim 10, wherein a distal end of the intraluminal member comprises a vein wall disruptor.

19. A method of treating a vein comprising the following steps:
   advancing an elongated intraluminal member from an access site and into a vein;
   rotating the intraluminal member or portion thereof in a first direction with a motorized drive system coupled to the intraluminal member or portion thereof, the motorized drive system comprising a motor drive circuit and a motor; and
   periodically changing the direction of rotation of the intraluminal member or portion thereof to perform rotational oscillation by periodically changing the direction of rotation of the motorized drive system,
   wherein the periodic changing of the direction of rotation of the intraluminal member occurs at defined time intervals, and
   wherein the rotational oscillation of the intraluminal member or portion thereof damages an inner wall of the vein, and inhibits entanglement of the intraluminal member or portion thereof with the inner wall of the vein.

20. The method of claim 19, wherein the motor comprises a reversible motor.

21. The method of claim 19, wherein the drive system comprises a kinematic chain.

22. The method of claim 19, wherein the drive system comprises a gearbox.

23. The method of claim 20, further comprising periodically reversing a rotation direction of the reversible motor.

24. The method of claim 23, further comprising programming a motor control and the motor drive circuit to perform the periodic reversal of the rotation direction of the reversible motor.

25. The method of claim 19, further comprising injecting sclerosant into the vein and onto the inner wall of the vein.

26. The method of claim 19, wherein a distal end of the intraluminal member comprises a vein wall disruptor.

* * * * *